United States Patent [19]
Alvarado et al.

[11] Patent Number: 5,808,105
[45] Date of Patent: Sep. 15, 1998

[54] 4-PHENOXYCOUMARINS AS HERBICIDAL AGENTS

[75] Inventors: Sergio I. Alvarado, Trenton; Pierre A. Marc, Willingboro; Brian J Dahlke, Morrisville; Eileen Reilly-Horch, Flemington, all of N.J.

[73] Assignee: American Cyanamid Company, Madison, N.J.

[21] Appl. No.: 821,494

[22] Filed: Mar. 21, 1997

Related U.S. Application Data

[62] Division of Ser. No. 515,846, Oct. 10, 1995, Pat. No. 5,681,968.

[51] Int. Cl.[6] .......................... C07D 311/18; A01N 43/16
[52] U.S. Cl. ............................................. 549/285; 504/292
[58] Field of Search ............................. 549/285; 504/292

[56] References Cited

U.S. PATENT DOCUMENTS 5,563,280  10/1996  Alvarado et al. ....................... 549/285

*Primary Examiner*—Ba K. Trinh
*Attorney, Agent, or Firm*—Gregory M. Hill, Esq.

[57] ABSTRACT

There are provided methods to control mono-cotyledenous weed species in the presence of crops and particularly in the presence of cereal crops. Also provided are 4-(2,6-disubstituted-phenoxy)coumarin derivatives useful as herbicidal agents and methods to prepare same.

8 Claims, No Drawings

4-PHENOXYCOUMARINS AS HERBICIDAL AGENTS

This is a divisional of application Ser. No. 08/515,846 filed on Oct. 10, 1995, now U.S. Pat. No. 5,681,968.

BACKGROUND OF THE INVENTION

The selective control of weeds is a constant problem in crop production around the world. In particular the control of monocotyledenous weeds when growing in the presence of monocotyledenous crops such as cereal crops is burdensome. Not only do said weed species tend to proliferate under the same or similar cultivation conditions in which cereal crops flourish, but in addition, the very herbicidal agents which are most effective for controlling these weeds, also tend to cause harmful phytotoxic effects to cereal crop plants. Therefore, new effective methods for the selective control of unwanted monocotyledenous weeds in cereal crop production are continually sought.

It is an object of this invention to provide methods for the effective control of monocotyledenous weeds in the presence of crop plants, including monocotyledenous crop plants, without undue harm to said crop plants.

It is a further object of this invention to provide 4-(2,6-disubstituted-phenoxy)coumarin derivatives, useful as selective herbicides in crop production and particularly in cereal crop production.

It is an advantage of this invention that the 4-(2,6-disubstituted-phenoxy)coumarin derivatives are particularly effective for controlling grass and other monocotyledenous weeds under flooded paddy rice application conditions while having little or no phytotoxic effects on the rice crop.

SUMMARY OF THE INVENTION

The present invention relates to a method for the control of monocotyledenous annual, perennial and aquatic plant species which comprises applying to the soil or water containing the seeds or other propagating organs of said plant species a herbicidally effective amount of a compound of formula I

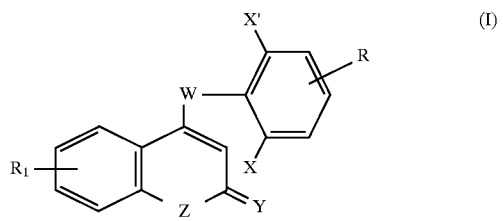

wherein
X and X' are each independently halogen, $C_1$–$C_4$alkyl or $C_2$–$C_4$alkenyl;
W, Y and Z are each independently O or S;
R is any combination of from one to three H, halogen, $C_1$–$C_4$ alkyl, $C_3$–$C_6$ cycloalkyl, $C_1$–$C_4$ haloalkyl or $C_1$–$C_4$ alkoxy groups;
$R_1$ is any combination of from one to four H, halogen, OH, CN, $NO_2$, SH, $C_1$–$C_6$ alkyl optionally substituted with one or more halogen or $OR_2$ groups,
$C_3$–$C_6$ cycloalkyl, $C_1$–$C_6$ alkylthio, $C_2$–$C_6$ alkenyl, $C_2$–$C_6$ halo-alkenyl, $C_2$–$C_6$ alkynyl, $C_2$–$C_6$ haloalkynyl, $OR_2$, $OCH_2COOR_3$, $OCH_2OR_4$, $OCOOR_5$, $OCONHR_6$, $OCOR_7$, $S(O)_nR_8$, $COR_9$, $CH(OR_{10})_2$, phenyl optionally substituted with one to three halogen, CN, $C_1$–$C_4$ alkyl, $C_1$–$C_4$ haloalkyl, $C_1$–$C_4$ alkoxy or $C_1$–$C_4$ haloalkoxy groups,
or benzyl optionally substituted with one to three halogen, CN, $C_1$–$C_4$ alkyl, $C_1$–$C_4$ haloalkyl or $C_1$–$C_4$ alkoxy groups;
$R_2$ is H, $C_1$–$C_4$ alkyl, $C_1$–$C_4$ haloalkyl, $C_2$–$C_6$ alkenyl, $C_2$–$C_6$ alkynyl, $C_2$–$C_6$ haloalkenyl or $C_2$–$C_6$ haloalkynyl;
$R_3$, $R_4$, $R_5$, $R_6$, and $R_7$ are each independently H, $C_1$–$C_4$ alkyl, $C_1$–$C_4$ haloalkyl, $C_3$–$C_6$ cycloalkyl, phenyl optionally substituted with one to three halogen, CN, $C_1$–$C_4$ alkyl, $C_1$–$C_4$ haloalkyl, $C_1$–$C_4$ alkoxy or $C_1$–$C_4$ haloalkoxy groups,
or benzyl optionally substituted with one to three halogen, $C_1$–$C_4$ alkyl, $C_1$–$C_4$ haloalkyl or $C_1$–$C_4$ alkoxy groups;
$R_8$ is $C_1$–$C_4$ alkyl, $C_1$–$C_4$ haloalkyl or phenyl optionally substituted with one to three halogen, CN, $C_1$–$C_4$alkyl, $C_1$–$C_4$haloalkyl, $C_1$–$C_4$alkoxy or $C_1$–$C_4$haloalkoxy groups;
$R_9$ is H, OH, $C_1$–$C_4$alkyl, $C_1$–$C_4$alkoxy, phenyl optionally substituted with one to three halogen, CN, $C_1$–$C_4$alkyl, $C_1$–$C_4$haloalkyl, $C_1$–$C_4$alkoxy or $C_1$–$C_4$haloalkoxy groups,
benzyl optionally substituted with one to three halogen, $C_1$–$C_4$alkyl, $C_1$–$C_4$haloalkyl, $C_1$–$C_4$alkoxy or $C_1$–$C_4$haloalkoxy groups
or $NR_{11}R_{12}$;
$R_{10}$ is H, $C_1$–$C_4$alkyl or —$(CH_2)_m$—;
$R_{11}$ and $R_{12}$ are each independently H, $C_1$–$C_4$alkyl, $C_2$–$C_4$alkenyl or $R_{11}$ and $R_{12}$ may be taken together with the atoms to which they are attached to form a 5- or 6-membered ring optionally interrupted by oxygen;
n is an integer of 0, 1 or 2 and
m is an integer of 2 or 3.

The invention also relates to the selective control of monocotyledenous weed species in the presence of crops which comprises applying to the soil or water in which the seeds or propagating organs of the weed species are located and in which the crop has been planted or transplanted a herbicidally effective amount of a compound of formula I as described hereinabove.

The invention further relates to herbicidal compounds of formula I, compositions containing same, and a method to prepare said compounds.

DETAILED DESCRIPTION OF THE INVENTION

Crop production can be reduced by as much as 30% to 60% by the presence of persistent and pestiferous weed species. A particular weed problem in raising and harvesting a variety of crops, particularly cereal crops, is monocotyledenous weed species such as monochoria, saggitaria, sedges and grasses. This is a persistent problem in the production of cereals such as corn, wheat, barley, rice, rye and the like. Most particularly, the presence and proliferation of grass weeds such as barnyardgrass and watergrass in rice cultivation can significantly lower crop yields and quality. The problem is further complicated because, in general, those agents which control monocotyledenous plants inherently cause phytotoxic damage to cereal crops.

It has now been found that monocotyledenous, annual, perennial and aquatic, weed species such as monochoria, saggitaria, sedges and grasses are effectively controlled by the application of 4-phenoxycoumarin derivatives of formula I to the soil or water in which the seeds or propagating organs are located.

surprisingly, said monocotyledenous weeds may be selectively controlled in the presence of cereal crops such as corn, wheat, barley, rice, rye and the like with little or no phytotoxic injury to said crops. Advantageously, 4-phenoxycoumarins of formula I may be applied preemergence to the monocotyledenous weeds and post-transplant to the rice crop seedlings under flooded paddy conditions to give effective weed control with little or no commensurate injury to the rice crop plants.

The 4-phenoxycoumarin derivatives of the invention which are useful as herbicidal agents are those compounds of formula I

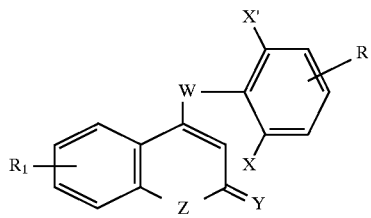
(I)

wherein
- X and X' are each independently halogen, $C_1$–$C_4$alkyl or $C_2$–$C_4$alkenyl;
- W, Y and Z are each independently O or S;
- R is any combination of from one to three H, halogen, $C_1$–$C_4$ alkyl, $C_1$–$C_6$ alkylthio, $C_3$–$C_6$ cycloalkyl, $C_1$–$C_4$ haloalkyl or $C_1$–$C_4$ alkoxy groups;
- $R_1$ is any-combination of from one to four H, halogen, OH, CN, $NO_2$, SH, $C_1$–$C_6$ alkyl optionally substituted with one or more halogen or $OR_2$ groups, $C_3$–$C_6$ cycloalkyl, $C_1$–$C_6$ alkylthio, $C_2$–$C_6$ alkenyl, $C_2$–$C_6$ haloalkenyl, $C_2$–$C_6$ alkynyl, $C_2$–$C_6$ haloalkynyl, $OR_2$, $OCH_2COOR_3$, $OCH_2OR_4$, $OCOOR_5$, $OCONHR_6$, $OCOR_7$, $S(O)_nR_8$, $COR_9$, $CH(OR_{10})_2$, phenyl optionally substituted with one to three halogen, CN, $C_1$–$C_4$ alkyl, $C_1$–$C_4$ haloalkyl, $C_1$–$C_4$ alkoxy or $C_1$–$C_4$ haloalkoxy groups,
  or benzyl optionally substituted with one to three halogen, CN, $C_1$–$C_4$ alkyl, $C_1$–$C_4$ haloalkyl or $C_1$–$C_4$ alkoxy groups;
- $R_2$ is H, $C_1$–$C_4$ alkyl, $C_1$–$C_4$ haloalkyl, $C_2$–$C_6$ alkenyl, $C_2$–$C_6$ alkynyl, $C_2$–$C_6$ haloalkenyl or $C_2$–$C_6$ haloalkynyl;
- $R_3$, $R_4$, $R_5$, $R_6$ and $R_7$ are each independently H, $C_1$–$C_4$ alkyl, $C_1$–$C_4$ haloalkyl, $C_3$–$C_6$ cycloalkyl, phenyl optionally substituted with one to three halogen, CN, $C_1$–$C_4$ alkyl, $C_1$–$C_4$ haloalkyl, $C_1$–$C_4$ alkoxy or $C_1$–$C_4$ haloalkoxy groups,
  or benzyl optionally substituted with one to three halogen, $C_1$–$C_4$ alkyl, $C_1$–$C_4$ haloalkyl or $C_1$–$C_4$ alkoxy groups;
- $R_8$ is $C_1$–$C_4$ alkyl, $C_1$–$C_4$ haloalkyl or phenyl optionally substituted with one to three halogen, CN, $C_1$–$C_4$alkyl, $C_1$–$C_4$haloalkyl, $C_1$–$C_4$alkoxy or $C_1$–$C_4$haloalkoxy groups;
- $R_9$ is H, OH, $C_1$–$C_4$alkyl, $C_1$–$C_4$alkoxy, phenyl optionally substituted with one to three halogen, CN, $C_1$–$C_4$alkyl, $C_1$–$C_4$haloalkyl, $C_1$–$C_4$alkoxy or $C_1$–$C_4$haloalkoxy groups,
  or benzyl optionally substituted with one to three halogen, $C_1$–$C_4$alkyl, $C_1$–$C_4$haloalkyl, $C_1$–$C_4$alkoxy or $C_1$–$C_4$haloalkoxy groups
  or $NR_{11}R_{12}$;
- $R_{10}$ is H, $C_1$–$C_4$alkyl or —$(CH_2)_m$—;
- $R_{11}$ and $R_{12}$ are each independently H, $C_1$–$C_4$alkyl, $C_2$–$C_4$alkenyl or $R_{11}$ and $R_{12}$ may be taken together with the atoms to which they are attached to form a 5- or 6-membered ring optionally interrupted by oxygen;
- n is an integer of 0, 1 or 2 and
- m is an integer of 2 or 3.

It is understood that R and $R_1$ represent substituents on the phenyl ring in positions 3, 4 and 5 (in the case of R) and on the fused benzene ring in positions 5, 6, 7 and 8 (in the case of $R_1$). In each instance the aromatic ring may range from being fully substituted to being fully unsubstituted (in the case of $R_1$) or disubstituted by X and X' (in the case of R). When the phenyl ring is disubstituted with X and X', then R is designated H. When the fused benzene ring position of the 4-phenoxycoumarin of formula I is fully unsubstituted, then $R_1$ is designated H.

The term haloalkyl designates an alkyl group, $C_nH_{2n+1}$, containing from one halogen atom to 2n+1 halogen atoms. Halogen atoms are Cl, Br, F or I.

Preferred compounds of formula I are those wherein X and X' are each independently Cl, Br, or $CH_3$ and W, Y and Z are O. More preferred compounds are those wherein X and X' are each independently Cl, Br or $CH_3$; W, Y and Z are O; R is H and $R_1$ is one, two or three halogen, $C_1$–$C_4$ alkyl, $C_1$–$C_4$ haloalkyl, $C_1$–$C_4$ alkoxy, $C_1$–$C_4$ haloalkoxy or $NO_2$ groups. Particularly preferred compounds are those wherein X and X' are each independently Cl, Br or $CH_3$; W, Y and Z are O; R is H and $R_1$ is 5-$C_1$–$C_4$ alkyl, 5-halogen, 5-$C_1$–$C_4$ haloalkyl or 5-$NO_2$.

The 4-(2,6-disubstituted-phenoxy)coumarin compounds of formula I may be prepared from readily available 2-hydroxyacetophenones of formula III or their salicylic acid precursors of formula II. The formula II acid may be converted to the corresponding acetophenone of formula III in the presence of methyl lithium using standard literature procedures such as that described by Heimark et al in the Journal of Labelled Compounds and Radiopharmaceuticals, 1986, Vol. 23, No. 2. The formula III acetophenone may be reacted with ethyl carbonate in the presence of at least 2 molar equivalents of a base such as sodium hydride to give the 4-hydroxycoumarin of formula IV. Said hydroxycoumarin may then be converted to the corresponding 4-chlorocoumarin derivative of formula V, using standard procedures such as $POCl_3$ plus an amine scavenger. The formula V chlorocoumarin is then reacted with a 2,6-disubstituted-phenol or thiophenol of formula VI to give the desired formula I product wherein Y is oxygen (formula Ia). To obtain those formula I products wherein Y is sulfur (Ib), the coumarin of Ia may be reacted with Lawesson's reagent or $P_2S_5$. The reaction scheme is shown in Flow Diagram I.

FLOW DIAGRAM I

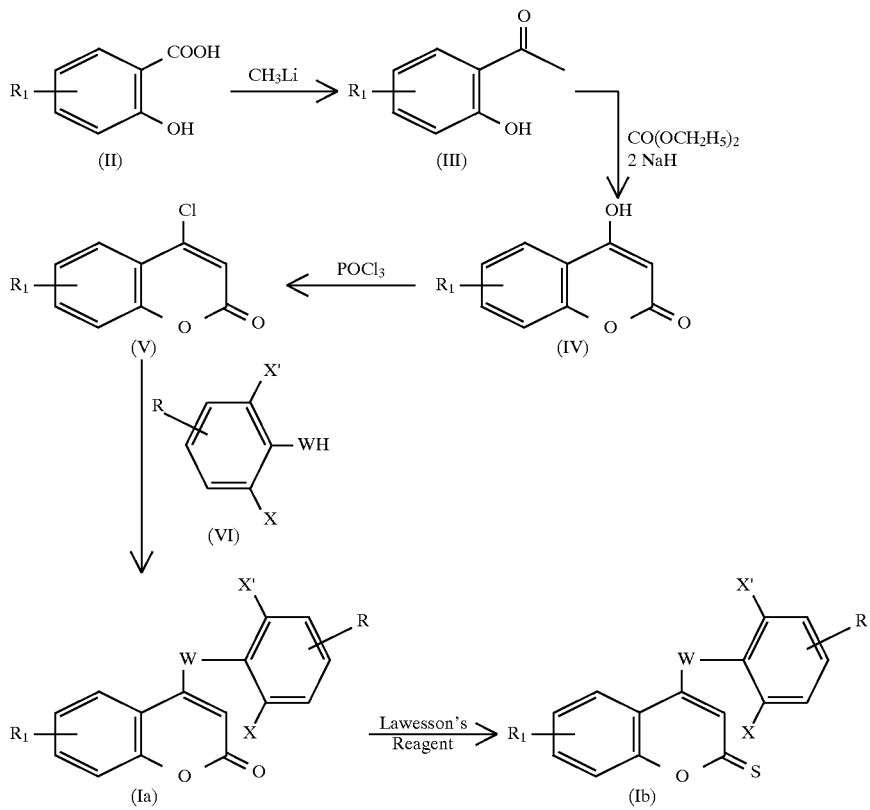

Alternatively, the formula II salicylic acid may be converted to the corresponding formula VII acid chloride. The acid chloride may be treated with ethyl malonate in the presence of a base as described in Journal of Medicinal Chemistry, 1975, Vol. 18, No. 4, pp. 391–394 by D. R. Buckle et al, to form an intermediate which is decarboxethoxylated by heating, optionally in the presence of a solvent, to afford the desired 4-hydroxycoumarin of formula IV. The formula IV hydroxycoumarin may be converted to 4-(2,6-disubstituted-phenoxy)coumarin compounds of formula I as shown hereinabove in Flow Diagram I. The reaction sequence is illustrated in Flow Diagram II.

FLOW DIAGRAM II

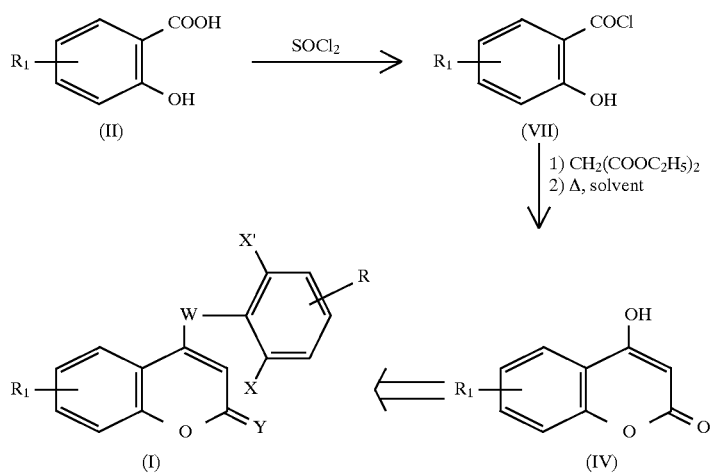

The 4-(2,6-disubstituted phenoxy)coumarin herbicidal agents of formula I may also be effectively prepared from phenols of formula VIII by treatment with dimethyl acetylenedicarboxylate as described by H. Cairns, et al in the Journal of Medicinal Chemistry, 1972, Vol. 15, No. 6, pp. 583–589, to give the formula IX fumaric acid. Surprisingly, treatment of the formula IX fumaric acid with a mixture of phosphorous pentoxide and methane sulfonic acid affords the formula X chromone-2-carboxylic acid in high yield. The formula X intermediate may then be converted to the formula V chlorocoumarin by treatment with thionyl chloride in the presence of a catalytic amount of dimethyl formamide as described by V. A. Zagorevskii and E. K. Orlova in Zhurnal Obschei Khimii, Vol. 33, No. 6, 963, pp. 1857–1863. The thus-prepared 4-chloro-coumarin may be employed to give the desired 4-(2,6-disubstituted phenoxy) coumarins of formula I as described hereinabove in Flow Diagram I. The reaction sequence is illustrated in Flow Diagram III.

plants such as corn, wheat, rye, barley, rice and the like. More particularly, the formula I compounds are especially valuable for controlling grass weeds in the presence of transplanted rice plants under flooded paddy conditions.

In actual agronomic practice, the compounds of the invention are applied in the form of a composition comprising an agronomically acceptable solid or liquid carrier and an herbicidally effective amount of a formula I phenoxycoumarin compound. For example, application may be in the form of liquid compositions such as suspension concentrates, aqueous concentrates, emulsifiable concentrates, concentrated emulsions and the like or in the form of solid compositions such as wettable powders, dispersible granulars, granular formulations, dusts and the like.

FLOW DIAGRAM III

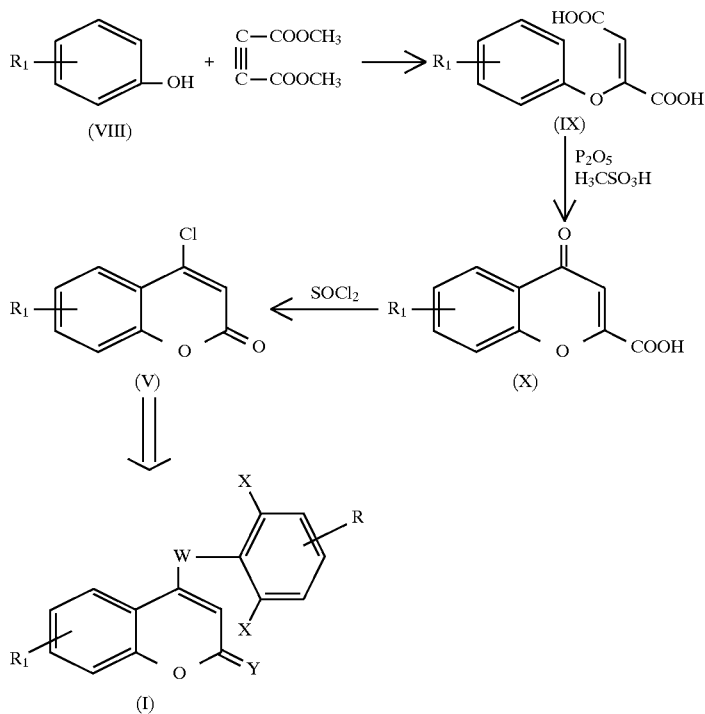

The 4-phenoxycoumarin compounds of the present invention are those compounds of formula I wherein X, X', W, Y, R and $R_1$ are as described hereinabove with the proviso that at least one of $R_1$, must be other than H. Said compounds are effective herbicidal agents useful for the control of a variety of monocotyledenous annual and perennial weed species. Moreover, these compounds are effective for the control of weeds indigenous to both dry land and wet land areas. Effective control may be obtained with application rates of about 0.006 kg/ha to 4.0 kg/ha, preferably about 0.06 kg/ha to 2.0 kg/ha. It is, of course, clear that rates above 4.0 kg/ha may be used to effectively control undesirable monocotyledenous weed species; however, rates of application of herbicide above the required effective level should be avoided since application of excessive amounts of herbicide is costly and serves no useful function in the environment.

Surprisingly, it has been found that the formula I phenoxycoumarin compounds of the invention are selective herbicides, useful in crop production. In particular, the formula I compounds are effective for controlling pestiferous monocotyledenous weeds such as grasses, sedges, monochoria and saggitaria in the presence of cereal crop It is contemplated the compounds of the invention be applied in combination with other pesticides either sequentially or concurrently as a tank mixture or as a single combination composition. In particular the combination application of a formula I phenoxycoumarin with a co-herbicide such as a sulfamoylurea, sulfonyl-urea, dinitroaniline, imidazolinone, thiocarbamate, azolopyrimidine sulfonamide, α-haloacetamide and the like. Of particular interest are combinations comprising a formula I phenoxycoumarin and a sulfamoylurea, a dinitroaniline, a sulfonylurea, or an imidazolinone. While not required, the combination composition comprising a formula I compound and a co-herbicide may also comprise other components, for example, fertilizers, inert formulation aides such as surfactants, emulsifiers, defoamers, dyes, extenders and the like.

For a more clear understanding of the invention, specific examples thereof are set forth below. The invention described and claimed herein is not to be limited in scope by these merely illustrative examples. Indeed, various modifications of the invention in addition to those exemplified and described herein will become apparent to those skilled in the

EXAMPLE 1
Preparation of 2-hydroxy-3-methoxyacetophenone

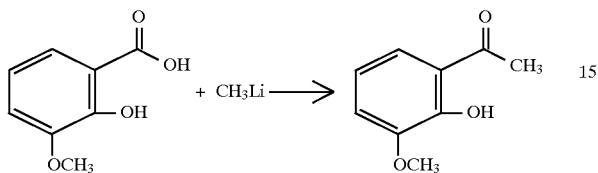

A mixture of 3-methoxysalicylic acid (4.0 g, 24 mmole) in tetrahydrofuran, under nitrogen, is treated dropwise with methyl lithium (56 mL of 1.4M solution in ether, 78.4 mmole) at a rate sufficient to maintain reflux temperature. The reaction mixture is stirred at reflux temperature for 17 hours, cooled to room temperature and poured over a mixture of brine, ice and 6N HCl. The resultant mixture is extracted with ethyl acetate. The organic extracts are combined, washed with brine, dried over $Na_2SO_4$ and filtered. The filtrate is concentrated in vacuo to give a dark orange residue which is taken up in 1:2 ethyl acetate:hexane, filtered through a silica gel plug and re-evaporated to give a residue. This residue is crystallized from cyclohexane to give the title product as yellow needles, 2.08 g (53% yield), mp 49°–51° C., identified by HPLC, $^1$HNMR and mass spectral analyses.

EXAMPLE 2
Preparation of 8-methoxy coumarin

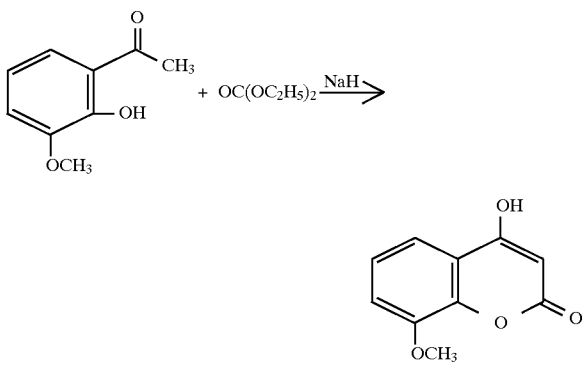

A stirred mixture of NaH(0.58 g 60% NaH, 14.5 mmole) and ethyl carbonate (2.84 g; 24 mmole) in chloroform, under $N_2$, is treated dropwise with a solution of 2-hydroxy-3-methoxyacetophenone (0.80 g, 4.8 mmole) in chloroform, heated at reflux temperature for 40 hours, cooled to room temperature, treated with about 45 mL 1N NaOH and stirred vigorously for 24 h. The phases are separated and the aqueous phase is acidified with 6N HCl. The resultant precipitate is filtered, washed with water and dried to give the title product as a white solid, 0.88 g (96% yield), identified by $^1$HNMR analysis.

EXAMPLE 3
Preparation of 4-chloro-6-methoxycoumarin

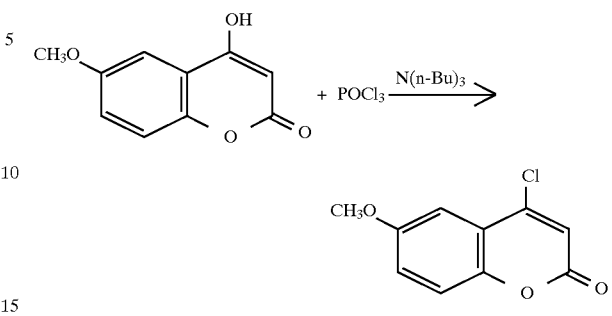

A stirred mixture of 4-hydroxy-6-methoxycoumarin (116 g, 0.603 mole) and $POCl_3$ (462.29 g, 3.015 mole) in toluene is treated dropwise with tri-n-butylamine (250 mL, 1.73 mole) at 25° C., heated at 100°–110° C. and monitored by HPLC analysis. When the reaction is complete, the mixture is cooled to room temperature, poured over ice, stirred mechanically for about 2 hours and filtered. The filtercake is washed with water and toluene, dissolved in methylene chloride and filtered through diatomaceous earth. The methylene chloride filtrate is concentrated and treated with a mixture of dimethylformamide and acetonitrile to afford crystallization. The mixture is filtered to give the title product, 81.7 g, (64% yield) identified by HPLC analysis.

EXAMPLE 4
Preparation of 4-(2,6-dichlorophenoxy)-6-methoxycoumarin

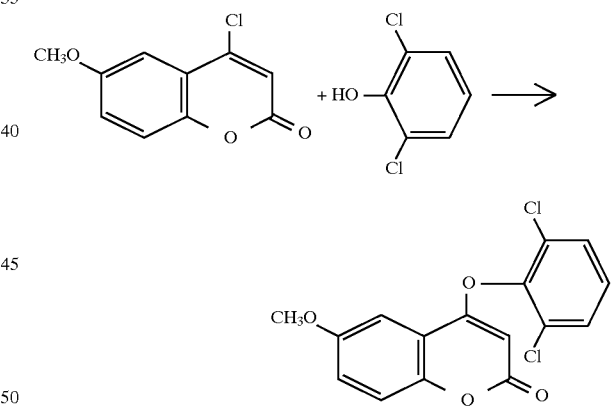

A stirred mixture of 4-chloro-6-methoxycoumarin (1.0 g, 4.75 mmole), 2,6-dichlorophenol (0.85 g, 5.22 mmole) and $K_2CO_3$ (0.98 g, 7.12 mmole) in acetonitrile, under $N_2$, is heated at reflux temperature for 16 hours, cooled to room temperature and poured into ice water. This mixture is extracted several times with ether. The extracts are combined and concentrated in vacuo to give a tan solid residue. The residue is crystallized from ethyl acetate/hexane to afford the title product as tan crystals, 1.17 g (73% yield), mp 170°–171° C., identified by IR, $^1$HNMR, $^{13}$CNMR, and mass spectral analyses.

EXAMPLE 5
Preparation of 4-(2-6-dichlorophenoxy)-6-hydroxycoumarin

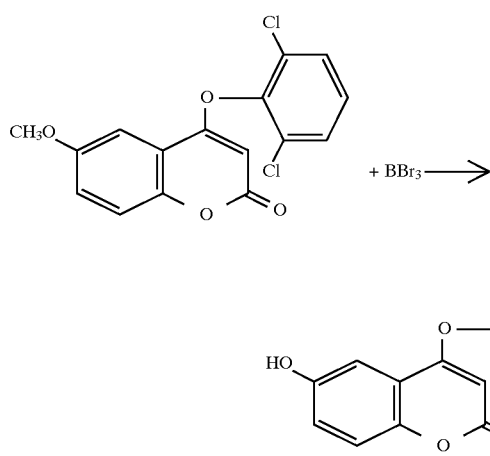

A solution of 4-(2,6-dichlorophenoxy)-6-methoxycoumarin (25 g, 0.074 mol) in methylene chloride, under $N_2$, is treated dropwise with 296 mL of a 1.0M solution of $BBr_3$ in methylene chloride at −70° C. When addition is complete, the dry ice/acetone cooling is removed and the reaction is allowed to come to room temperature over a 16 hour period. The reaction mixture is diluted with additional methylene chloride, poured into ice water with mechanical stirring and filtered to give a pale yellow solid filtercake. The solid is air-dried and crystallized from dimethylformamide/acetonitrile/water (1:1:0.1) to afford the title product as white crystals, 19.7 g (86% yield), mp>250° C. identified by $^1$HNMR analysis.

EXAMPLE 6
Preparation of 4-(2,6-dichlorophenoxy)-6-(difluoromethoxy)coumarin

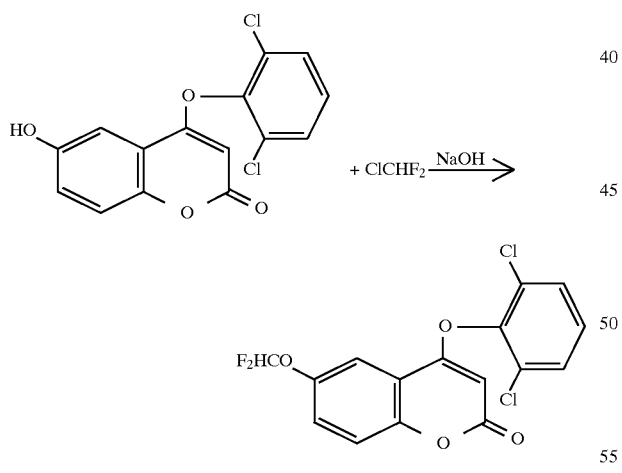

A stirred suspension of 4-(2,6-dichlorophenoxy)-6-hydroxycoumarin (1.3 g, 3.71 mmole) in acetone is bubbled through with chlorodifluoromethane at room temperature, under $N_2$, for about 30–45 minutes, cooled to 5°–10° C., treated with 50% NaOH solution (2.4 g, 1.2 g NaOH, 29.7 mmole NaOH), stirred for 2 hours at room temperature and filtered. The solid filtercake is washed with methylene chloride and crystallized from acetonitrile/methanol/water to afford the title product as a white solid, 0.959 (69% yield), mp 145°–148° C., identified IR, $^1$HNMR, $^{19}$FNMR, $^{13}$CNMR, and mass spectral analyses.

EXAMPLE 7
Preparation of 4-hydroxy-8-nitrocoumarin

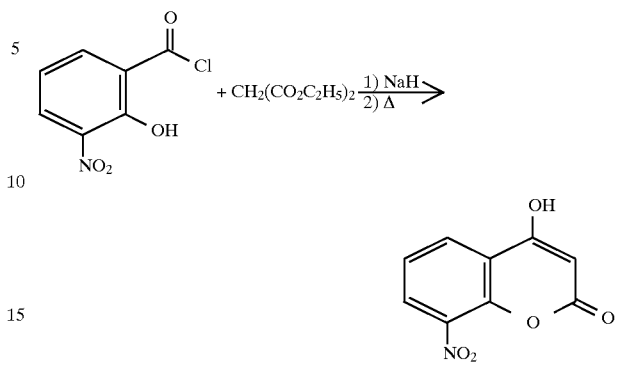

A solution of NaH (6.94 g, 0.291 mole) in dimethoxyethane is cooled using dry ice/acetone cooling, treated dropwise with diethyl malonate (46.6 g, 0.29 mole), allowed to warm to 0° C., treated dropwise with a solution of 3-nitrosalicylyl chloride (19.5 g, 0.10 mole) in dimethoxyethane, allowed to warm to room temperature, stirred for 3 hours at room temperature, heated at 60° C. until reaction is complete by HPLC analysis, cooled to room temperature, poured onto a mixture of ice water and methylene chloride and stirred for about 0.5 hour. The phases are separated, the aqueous phase is acidified with 50% HCl to pH 5 and filtered. The filtercake is dispersed in acetic acid, heated and filtered. This filtercake is air-dried and 8.6 g is dispersed in dimethyl sulfoxide, heated at 100° C. for about 2 hours, cooled to room temperature, poured onto ice water and filtered. The solid is taken up in acetonitrile, filtered hot, cooled and filtered to give the title product, mp 242°–245° C., identified by IR, $^1$HNMR and mass spectral analyses.

EXAMPLE 8
Preparation of 4-(2,6-dichlorophenoxy)-6-methoxythionocoumarin

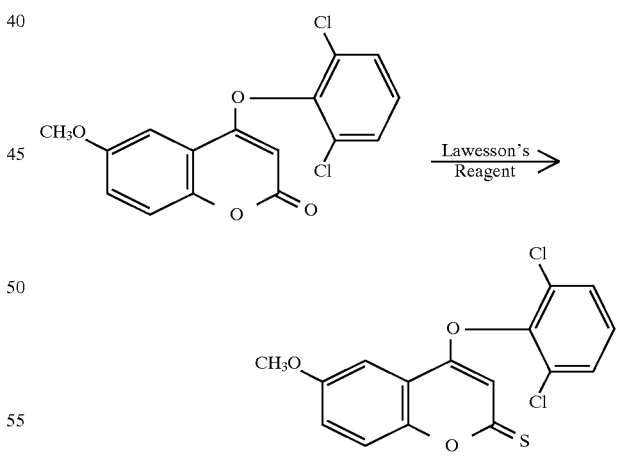

A mixture of 4-(2,6-dichlorophenoxy)-6-methoxycoumarin (0.40 g, 1.2 mmol) and Lawesson's Reagent[1] (0.53 g, 1.3 mmol) in dioxane is heated at reflux temperature, stirred for about 4 hours, cooled to room temperature, stirred at room temperature for 16 hours and filtered. The filtercake is washed with petroleum ether and air-dried to give the title product as a yellow solid, 0.28 g (57% yield), mp 231°–232° C., identified by $^1$HNMR, $^{13}$CNMR and mass spectral analyses. [1]Methoxyphenylthionophosphine sulfide dimer

EXAMPLES 9–15

Preparation of 4-phenoxythionocoumarin derivatives

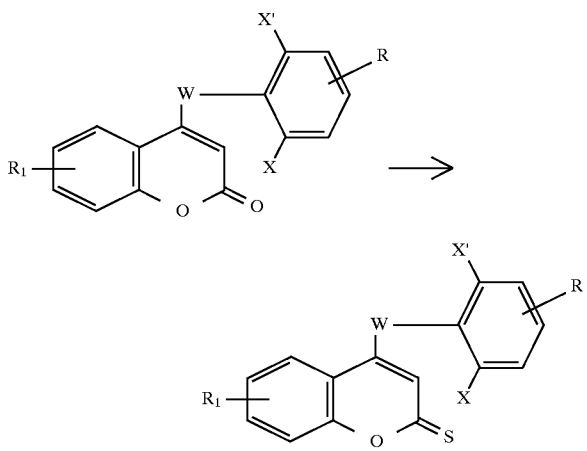

Using essentially the same procedure described in Example 8 and substituting the appropriate 4-phenoxycoumarin substrate, the following compounds are obtained.

TABLE I

| Example No. | X  | X' | R | W | $R_1$      |
|-------------|----|----|---|---|------------|
| 9           | Cl | Cl | H | O | 5-OH       |
| 10          | Br | Br | H | O | 7-OCH$_3$  |
| 11          | Cl | Cl | H | O | 7-OCH$_3$  |
| 12          | Cl | Cl | H | O | 6,7-di-OCH$_3$ |
| 13          | Cl | Cl | H | O | 7-NO$_2$   |
| 14          | Cl | Cl | H | O | 5-OC$_2$H$_5$ |
| 15          | Cl | Cl | H | O | 5-OCHF$_2$ |

EXAMPLE 16

Preparation of 4-(2,6-dichorophenoxy)-6-(N-methylcarbamoyl) coumarin

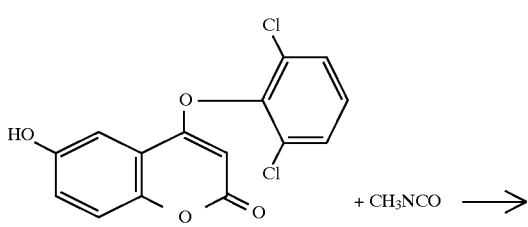

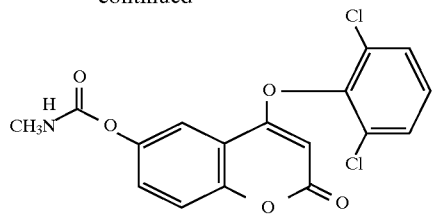

A solution of 4-(2,6-dichlorophenoxy)-6-hydroxycoumarin (0.5 g, 1.55 mmole) in dimethyl formamide, under nitrogen, at room temperature is treated with triethylamine (0.7 mL, 5 mmole), then treated with CH$_3$NCO (0.5 mL, 5.5 mmole) and allowed to stir at room temperature for about 1 hour. When the reaction is complete by HPLC analysis, the reaction mixture is poured onto water and extracted with methylene chloride. The extracts are concentrated in vacuo to give a residue. The residue is crystallized from methylene chloride/hexane to afford the title product as white crystals, 0.38$_2$ (71% yield), mp 292°–299° C., identified by $^1$HNMR, $^{13}$CNMR and IR analyses.

EXAMPLE 17

Preparation of 4-(2,6-dichlorophenoxy)-6-(methoxymethyloxy) coumarin

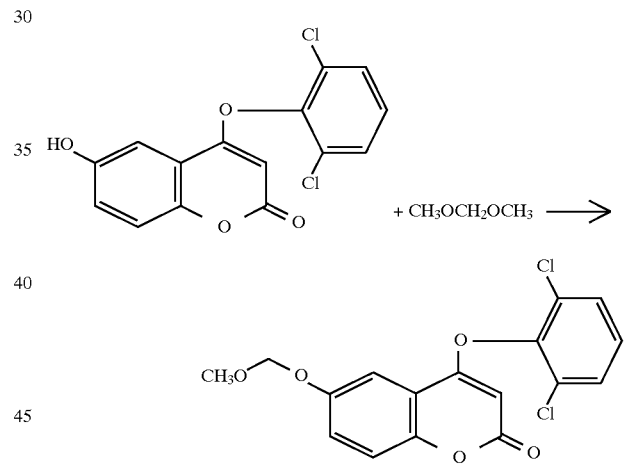

A mixture of 4-(2,6-dichlorophenoxy)-6-hydroxycoumarin (1.2 g, 3.2 mmole), dimethoxymethane (0.565 g, 7.4 mmole), POCl$_3$ (0.74 g, 4.8 mmole) and dimethylformamide (0.43 g, 5.94 mmole) in toluene is heated at 90°–100° C. for 4 hours, cooled to room temperature, poured onto ice water and filtered. The filter-cake is dried and recrystallized from acetonitrile/water to afford the title product, 0.45 g (38% yield), mp 302°–305° C. (dec), identified by $^1$HNMR, $^{13}$CNMR and IR analyses.

EXAMPLE 18

Preparation of 2-hydroxy-4,5-dimethoxyacetophenone

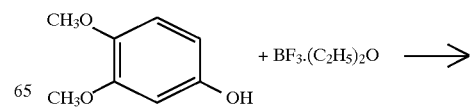

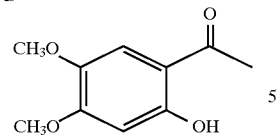

A solution of 3,4-dimethoxyphenol (0.50 g, 3.24 mmole) in acetic acid is treated with boron trifluoride etherate (1.20 ml, 9.72 mmole) at 25° C., heated at reflux temperature until reaction is complete by thin layer chromatographic analysis, cooled to room temperature and poured onto ice water. The resultant mixture is filtered, the filtercake is washed with water and ether and dried in vacuo to give the title product as an orange powder, 0.64 g (100% yield), identified by $^1$HNMR.

EXAMPLE 19

Preparation of 2-[4-(trifluoromethoxy)phenoxy]fumaric acid

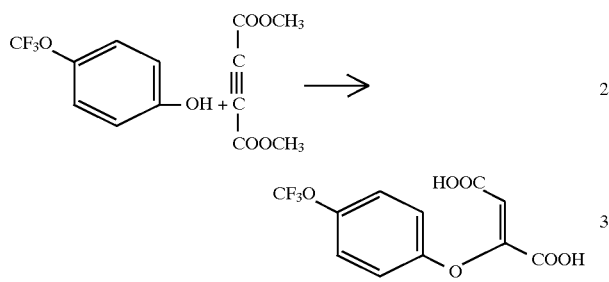

A mixture of 4-(trifluoromethoxy)phenol (2.75 g, 12.5 mmole) and dimethyl acetylene dicarboxylate (1.69 ml, 13.7 mmole) in dioxane is treated with benzyltrimethylammonium hydroxide (0.15 ml, 40% aqueous) at room temperature under a nitrogen atmosphere, heated to 90°–95° C. (condensation complete by thin layer chromatographic analysis) cooled to 40° C., treated with sodium hydroxide (10 ml, 20% aqueous), heated at 90° C. for 1 hour and cooled to room temperature. The reaction mixture is treated with 10% aqueous HCl to pH 7 and filtered. The filtrate is acidified to about pH 1 with HCl to afford a yellow precipitate. The solid is filtered and dried to give the title product, 2.56 g (70% yield), mp 208°–210° C., identified by $^1$H, $^{13}$C and $^{19}$FNMR, mass spectral and elemental analyses.

EXAMPLE 20

Preparation of 6-(trifluoromethoxy)chromone-2-carboxylic acid

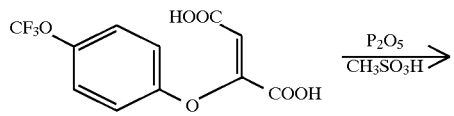

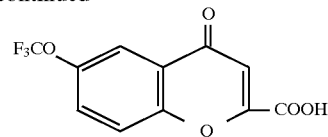

A solution of phosphorous pentoxide (1.17 g, 8.21 mmole) in methanesulfonic acid (14.38 g) is treated with 2-[4-(trifluoromethoxy)phenoxy]fumaric acid (2.00 g, 6.85 mmole), stirred for 16–18 hours at ambient temperatures and for 7 hours at 70° C., cooled to room temperature and poured onto ice. The resultant mixture is filtered and the filtercake is dried to afford the title product, 1.75 g, (93% yield), mp 192°–194° C., identified by $^1$H and $^{13}$CNMR, IR, mass spectral and elemental analyses.

EXAMPLE 21

Preparation of 4-chloro-6-(trifluoromethoxy)coumarin

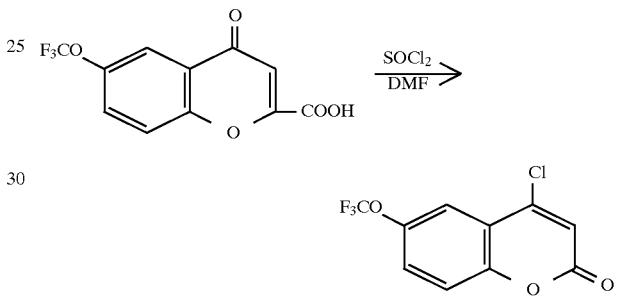

A stirred mixture of 6-(trifluoromethoxy)-chromone-2-carboxylic acid (1.50 g, 5.47 mmole) in thionyl chloride (6.0 ml) is treated with 1 drop of dimethyl formamide (DMF), heated at reflux temperature for 6 hours, cooled to room temperature and concentrated in vacuo. The residue is dispersed in toluene, treated with a saturated NaHCO$_3$ solution and stirred until neutralized. The phases are separated and the toluene phase is concentrated in vacuo. The resultant residue is purified in acetonitrile and methylene chloride to give the title product, 1.04 g, (72% yield), mp 85°–87° C., identified by $^1$H, $^{13}$C and $^{19}$FNMR, IR, mass spectral and elemental analyses.

EXAMPLE 22–95

Preparation of 4-(2,6-substituted-phenoxy)coumarin derivatives

Using essentially the same procedures described in Examples 1 through 21, the following 4-(2,6-disubstituted phenoxy) coumarin derivatives shown in Table II are obtained.

TABLE II

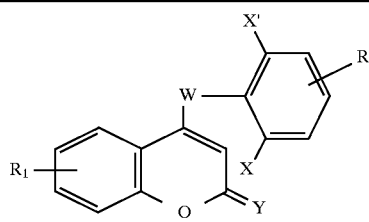

| Example No. | X | X' | R | W | Y | R₁ | mp °C. |
|---|---|---|---|---|---|---|---|
| 22 | Cl | Cl | H | O | O | H | 159 |
| 23 | F | F | H | O | O | H | 195.6 |
| 24 | Br | Br | H | O | O | H | 162–170 |
| 25 | CH₃ | CH₃ | H | O | O | H | 163–164 |
| 26 | F | OCH₃ | H | O | O | H | 145–146 |
| 27 | F | NO₂ | H | O | O | H | 203–205 |
| 28 | OCH₃ | OCH₃ | H | O | O | H | 175 |
| 29 | Cl | Cl | H | O | O | 6-(2Cl,4CF₃,6F—C₆H₂) | 155–157 |
| 30 | Cl | Cl | H | O | O | 6-CH₃ | 191–192 |
| 31 | Br | Br | H | O | O | 6-OCH₃ | 174–175 |
| 32 | Br | Br | H | O | O | 6-CH₃ | 182–183 |
| 33 | Cl | Cl | H | O | O | 6-(O—CONHC₂H₅) | 220–221 |
| 34 | OCH₃ | OCH₃ | H | O | O | 6-OCH3 | 206–208 |
| 35 | Cl | Cl | H | O | O | 7-OCH3 | 165–168 |
| 36 | OCH₃ | OCH₃ | H | O | O | 7-OCH3 | 205.5–207 |
| 37 | OCH₃ | OCH₃ | H | O | O | 5-OCH3 | 186.5–188.5 |
| 38 | Cl | Cl | H | O | O | 7-(OCH₂CH=CH₂) | 185.5–182 |
| 39 | Cl | Cl | H | O | O | 5-(OCH₂CH=CH₂) | 156.5–158.5 |
| 40 | Cl | Cl | H | O | O | 5-(OCH₂COOCH) | 161.2–162.6 |
| 41 | Cl | Cl | H | O | O | 6-(OCH₂COOCH) | 135–136 |
| 42 | Cl | Cl | H | O | O | 6-(OCH₂CH=CH₂) | 145–146 |
| 43 | Cl | Cl | H | O | O | 6-(OCH₂C≡CH) | 153 |
| 44 | Cl | Cl | H | O | O | 6-(OCH₂CH₂CF=CF₂) | 146 |
| 45 | Cl | Cl | H | O | O | 6-OCH(CH₃)₂ | 141 |
| 46 | Cl | Cl | H | O | O | 6-OCH(CH₃)C₂H₅ | 138 |
| 47 | Cl | Cl | H | S | O | 6-OCH₃ | 216–217 |
| 48 | Cl | Cl | H | O | O | 6-OSO₂CF₃ | 137 |
| 49 | Br | Br | H | O | O | 6-F | 165 |
| 50 | Cl | Cl | H | O | O | 6-C₂H₅ | 184 |
| 51 | Cl | Cl | H | O | O | 6-F | 183 |
| 52 | Cl | Cl | H | S | O | 6-F | 168 |
| 53 | Cl | Cl | H | S | O | 6-C₂H₅ | 182 |
| 54 | Cl | Cl | 4-Cl | O | O | 6,7-di-CH₃ | 264 |
| 55 | Br | Br | H | O | O | 6,7-di-OCH₃ | 191 |
| 56 | Cl | Cl | 4-F | O | O | 6-OCH₃ | 217 |
| 57 | Cl | Cl | H | O | O | 6-Cl | 204 |
| 58 | Br | Br | H | O | O | 6-Cl | 188 |
| 59 | Cl | Cl | H | S | O | 6-Cl | 214 |
| 60 | Cl | Cl | 4-Cl | O | O | 6-OCH₃ | 196 |
| 61 | Cl | Cl | 4-F | O | O | 6,7-di-CH₃ | 255 |
| 62 | Cl | Cl | H | O | O | 6-OCH₂CHF₂ | 167 |
| 63 | Cl | Cl | H | O | O | 6,7-di-CH₃ | 212 |
| 64 | Cl | Cl | H | S | O | 6,7-di-CH₃ | 246 |
| 65 | Cl | Cl | H | O | O | 6,7-di-OCH₃ | 191 |
| 66 | Cl | Cl | H | S | O | 6,7-di-OCH₃ | 172 |
| 67 | Cl | Cl | H | O | O | 6,8-di-Cl | 206 |
| 68 | Cl | Cl | H | S | O | H | 212 |
| 69 | Br | Br | H | O | O | 6-C₂H₅ | 159 |
| 70 | Br | Br | H | O | O | 6,7-di-CH₃ | 210 |
| 71 | Br | Br | H | O | O | 6,8-di-Cl | 218 |
| 72 | Cl | Cl | 4-F | O | O | 6-F | 187 |
| 73 | Cl | Cl | 4-Cl | O | O | 6-F | 208 |
| 74 | Cl | Cl | 4-F | O | O | 6,7-di-OCH₃ | 205 |
| 75 | Cl | Cl | 4-Cl | O | O | 6-Cl | 221 |
| 76 | Cl | Cl | 4-F | O | O | 6-Cl | 200 |
| 77 | Cl | Cl | H | O | O | 6-OC₂H₅ | 162 |
| 78 | F | F | 3,4,5-tri-F | O | O | 6-F | 173 |
| 79 | Br | Br | 4-CH₃ | O | O | 6,7-di-OCH₃ | 154 |
| 80 | Cl | Cl | H | O | O | 6-OCH₂C₆H₄OCF₃-p | 129 |
| 81 | Br | Br | 4-F | O | O | 6-OCH₃ | 200 |
| 82 | Br | Br | 4-Br | O | O | 6-OCH₃ | 195–197 |
| 83 | Cl | Cl | 3-Cl | O | O | 6-OCH₃ | 218–220 |
| 84 | F | F | H | O | O | 6-OCH₃ | 213–214 |
| 85 | Cl | Cl | H | O | O | 6-CN | 249–250 |

TABLE II-continued

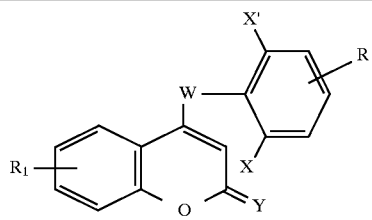

| Example No. | X | X' | R | W | Y | R₁ | mp °C. |
|---|---|---|---|---|---|---|---|
| 86 | Cl | Cl | H | O | O | 5,6,7-tri-OCH₃ | 169–170 |
| 87 | Cl | Cl | H | O | O | 5-OCH₃ | 203.6–207.5 |
| 88 | Cl | Cl | H | O | O | 7-OH | 263–264.5 |
| 89 | Cl | Cl | H | O | O | 5-OH | 250–256 |
| 90 | Cl | Cl | H | S | O | 5-OCH₃ | 204–205 |
| 91 | Br | Br | H | O | O | 5-OCH₃ | 201–203 |
| 92 | Cl | Cl | H | S | O | 8-OCH₃ | 183–185 |
| 93 | Br | Br | H | O | O | 8-OCH₃ | 157 |
| 94 | Cl | Cl | H | O | O | 8-OCH₃ | 142–144 |
| 95 | Br | Br | H | O | O | 5,6,7-tri-OCH₃ | 179–181 |
| 99 | Br | Br | H | O | O | 6-OH | 210 |
| 100 | Cl | Cl | H | O | O | 6-I | 266–267 |
| 101 | Br | Br | H | O | O | 6-OCHF₂ | 151–152 |
| 102 | Cl | Cl | H | O | O | 8-OCHF₂ | 198–201 |
| 103 | Br | Br | H | O | O | 8-OCHF₂ | 181–183 |
| 104 | Cl | Cl | H | O | O | 6-CH₂OCH₃ | 158 |
| 105 | Br | Br | H | O | O | 8-OH | 227 |
| 106 | Cl | Cl | H | O | O | 8-OH | 252 |
| 107 | CH₃ | CH₂CH=CH₂ | H | O | O | 6-OCH₃ | 88–90 |
| 108 | CH(CH₃)₂ | CH(CH₃)₂ | H | O | O | 6-OCH₃ | 129–131 |
| 109 | CH₃ | CH₃ | H | O | O | 6-OCH₃ | 192–193 |
| 110 | Cl | Cl | H | O | O | 6-OCF₃ | 172–175 |
| 111 | Cl | Cl | H | O | O | 6-CF₃ | 181–183 |
| 112 | Br | Br | H | O | O | 6-CH₂Br | 220 |
| 113 | Cl | Cl | H | O | O | 6-CHO | 200 |
| 114 | CH₃ | C(CH₃)₃ | H | O | O | 6-OCH₃ | 148–151 |
| 115 | Cl | Cl | H | O | O | 6-C₆H₅ | 146–152 |
| 116 | Cl | Cl | H | O | O | 6-COOH | 305 |
| 117 | Br | Br | H | O | O | 6-CHO | 185–197 |
| 118 | Cl | Cl | H | O | O | 6-OCH₂CH₂OC₂H₅ | 89–91 |
| 119 | Cl | Cl | H | O | O | 6-SCH₃ | 168–170 |
| 120 | Cl | CH₃ | H | O | O | 6-OCH₃ | 192 |
| 121 | Cl | CH₃ | H | O | O | 6,7-di-OCH₃ | 141 |
| 122 | Cl | CH₃ | H | O | O | 6,7-di-OCH₃ | 172–173 |
| 123 | Cl | CH₃ | H | O | O | 6-CH₃ | 186 |
| 124 | Cl | CH₃ | H | O | O | 6-C₂H₅ | 165–166 |
| 125 | Cl | CH₃ | H | O | O | 8-OCH₃ | 157–158 |
| 126 | CH₃ | CH₃ | H | O | O | 8-OCH₃ | 142–143 |
| 127 | Cl | Cl | H | O | O | 6,7-di-OH | >300 |
| 128 | CH₃ | n-C₃H₇ | H | O | O | 6-OCH₃ | — |
| 129 | CH₃ | CH₃ | H | O | O | 6-CF₃ | 193–194 |
| 130 | CH₃ | CH₃ | H | O | O | 6-OCF₃ | 162–164 |
| 131 | Cl | CH₃ | H | O | O | 8-CF₃ | 205–206 |
| 132 | Br | Br | 3,5-di-OCH₃ | O | O | 6-OCH₃ | 233–234 |
| 133 | Cl | CH₃ | H | O | O | 5,6,7-tri-OCH₃ | 143–144 |
| 134 | I | I | 4-I | O | O | 6-OCH₃ | 202–203 |
| 135 | Cl | Cl | H | O | O | 8-CF₃ | 217–218 |
| 136 | Cl | CH₃ | H | O | O | 5-OCH₃ | 172–173 |
| 137 | Cl | Cl | H | O | O | 5-CF₃ | 159–160 |
| 138 | Br | Br | H | O | O | 5-CF₃ | 179–189 |
| 139 | Cl | CH₃ | H | O | O | 5-CF₃ | 157–159 |
| 140 | Cl | Cl | H | O | O | 6-Cl,7-OCH₃ | 167–168 |
| 141 | Br | CH₃ | H | O | O | 6-OCH₃ | 180–181 |
| 142 | Cl | Cl | H | O | O | 6-C≡CH | 220–224 |
| 143 | Cl | CH₃ | H | O | O | 8-CH₃ | 174–175 |
| 144 | Cl | Cl | H | O | O | 7-OCHF₂ | 158–160 |
| 145 | Cl | CH₃ | H | O | O | 6-OCHF₂ | 158–161 |
| 146 | Cl | Cl | H | O | O | 7-CF₃ | 180–181 |
| 147 | Cl | CH₃ | H | O | O | 7-CF₃ | 146–148 |
| 148 | Cl | CH₃ | H | O | O | 7,8-di-OCH₃ | 179–181.5 |
| 149 | Cl | Cl | H | O | O | 5-OCH(CH₃)₂ | 158.5–162 |
| 150 | Cl | Cl | H | O | O | 5-OC₂H₅ | 152.5–155 |
| 151 | Cl | Cl | H | O | O | 5-OCHF₂ | 178.3–180 |
| 152 | Cl | Cl | H | O | O | 5-OCH₃,6-Cl | 176–178 |

TABLE II-continued

| Example No. | X | X' | R | W | Y | R₁ | mp °C. |
|---|---|---|---|---|---|---|---|
| 153 | Cl | Cl | H | O | O | 8-Cl | 206–208 |
| 154 | Cl | Cl | H | O | O | 5-OCOCH₃ | 130–133 |
| 155 | Cl | CH₃ | H | O | O | 5-Cl | 135–136 |
| 156 | Br | Br | H | O | O | 5-Cl | 155–156 |
| 157 | Cl | Cl | H | O | O | 5-Cl | 157–158 |
| 158 | Cl | Cl | H | O | O | 5-OCH₃,8-Cl | 213–215.5 |
| 159 | Cl | CH₃ | H | O | O | 5-CH₃,8-Cl | 175–176 |
| 160 | Cl | Cl | H | O | O | 5-CH₃,8-Cl | 166–167 |
| 161 | Cl | Cl | H | O | O | 5-OCOC(CH₃)₃ | 139–141 |
| 162 | Br | Br | H | O | O | 5-OCOCH₃ | 220–223 |
| 163 | Br | Br | H | O | O | 5-OCOC(CH₃)₃ | 218.3–220 |
| 164 | Cl | Cl | H | O | O | 7-OCOCH₃ | 182–183.5 |
| 165 | Cl | Cl | H | O | O | 7-OCOC(CH₃)₃ | 135–137 |
| 166 | Cl | Cl | H | O | O | 8-OCOCH₃ | 161–163 |
| 167 | Cl | Cl | H | O | O | 8-OCOC(CH₃)₃ | 144–146 |
| 168 | Cl | Cl | H | O | O | 5-F | 146–147 |
| 169 | Cl | CH₃ | H | O | O | 5-F | 137–138 |
| 170 | Cl | Cl | H | O | O | 5-CH₃ | 129–130 |
| 171 | Cl | CH₃ | H | O | O | 5-CH₃ | 118–119 |
| 172 | Cl | Cl | H | O | O | 5,7-di-Cl | 205–207 |
| 173 | Br | Br | H | O | O | 5,7-di-Cl | 208–209 |
| 174 | Cl | CH₃ | H | O | O | 5,7-di-Cl | 158–160 |
| 175 | Cl | Cl | H | O | O | 6,7-di-Cl | 195–196 |
| 176 | Cl | Cl | H | O | O | 5,6-di-Cl | 193–195 |
| 177 | Cl | CH₃ | H | O | O | 6,7-di-Cl | 210–212 |
| 178 | Br | Br | H | O | O | 6,7-di-CH₃ | 155–156 |
| 179 | Br | Br | H | O | O | 5,6-di-Cl | 209–211 |
| 180 | Br | Br | H | O | O | 6,7-di-Cl | 206–208 |
| 181 | Cl | Cl | H | O | O | 5,7-di-CH₃,6-Cl | 210–212 |
| 182 | Br | Br | H | O | O | 5,7-di-CH₃,6-Cl | 219–221 |
| 183 | Cl | CH₃ | H | O | O | 5,7-di-CH₃,6-Cl | 187–188 |
| 184 | Cl | Cl | H | O | O | 7,8-di-Cl | 212–214 |
| 185 | Br | Br | H | O | O | 7,8-di-Cl | 211–212 |
| 186 | Cl | CH₃ | H | O | O | 7,8-di-Cl | 234–236 |
| 187 | Cl | Cl | H | O | O | 5,7-di-Br,6-CH₃ | 217–218 |
| 188 | Cl | CH₃ | H | O | O | 5,7-di-Br,6-CH₃ | 201–203 |
| 189 | Cl | Cl | H | O | O | 5,8-di-Cl | 190–191 |
| 190 | Br | Br | H | O | O | 5,8-di-Cl | 203–205 |
| 191 | Cl | CH₃ | H | O | O | 5,8-di-Cl | 181–183 |
| 192 | Cl | Cl | H | O | O | 5-NO₂ | 211–212 |

EXAMPLE 193

Preparation of 4-hydroxy-5-(trifluoromethyl)dithiocoumarin.

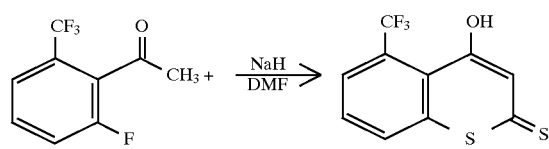

A mixture of 2'-fluoro-6'-(trifluoro-methyl)acetophenone (3.0 g, 14.5 mmol), carbon disulfide (1.5 mL, 26.7 mmol) and dimethylformamide (DMF) (12.5 mL) in benzene at 15°–25° C. is treated portion-wise with a 60% dispersion of sodium hydride in mineral oil (1.15 g, 28.8 mmol NaH) over a 1.5 hour period, stirred for 0.5 hour, heated at 125° C. for 1 hour, cooled to room temperature and diluted with water. The resultant mixture is treated with acetic acid and extracted with ether. The aqueous phase is acidified to pH 3 with HCl and extracted with ethyl acetate. The ethyl acetate extracts are combined, washed sequentially with water and brine, dried over MgSO₄ and concentrated in vacuo to give an orange oil residue. The residue is crystallized from diethyl ether/hexanes to give the title product as a white solid, 3.0 g (79% y), mp 142°–144° C., identified by IR, ¹HNMR, ¹⁹FNMR and mass spectral analyses.

EXAMPLE 194

Preparation of 4-(2,6-dichlorophenoxy)-5-trifluoro-methyl) dithiocoumarin.

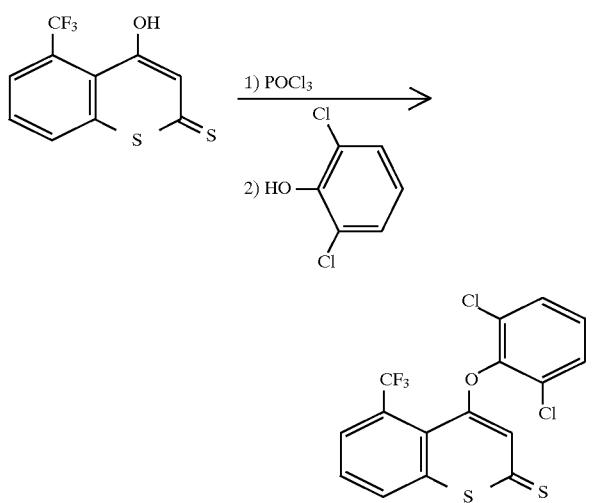

Using essentially the same procedures described in Examples 3 and 4 hereinabove, the title product is obtained and identified by IR, $^1$HNMR, $^{19}$FNMR and mass spectral analyses.

EXAMPLE 195

Preparation of 4-(2,6-dichlorophenoxy)-6-chlorodithiocoumarin.

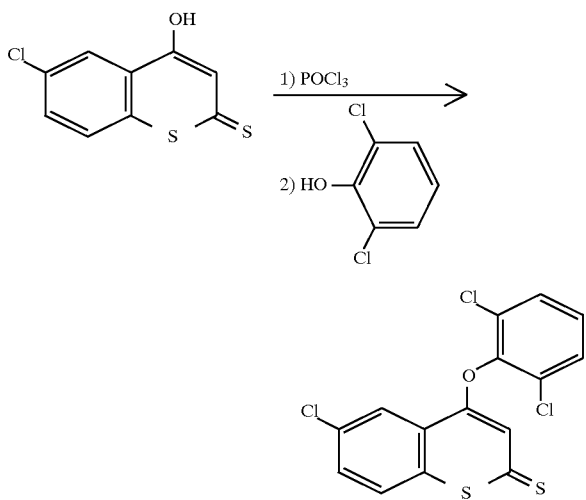

Using essentially the same procedures described hereinabove in Examples 3, 4 and 193, the title product is obtained, mp 208°–210° C., identified by IR, $^1$HNMR and mass spectral analyses.

EXAMPLE 196

Preemergence Herbicidal Evaluation Of Test Compounds In The Presence of Transplanted Rice Under Flooded Paddy Conditions The preemergence herbicidal activity and rice crop tolerance under post-transplant application conditions is determined in the following manner. Grass weed seeds or tubers are planted in the top 0.5 cm of silt loam soil in plastic containers with no drainage holes and 4–6 rice seedlings (CV. Tebonnet), at the two-leaf stage, are transplanted into the same containers. The plastic containers may be 32 oz. containers having a diameter of 10.5 cm or 13 cm×13 cm square by 8 cm deep. After seeding and transplanting, the containers are placed on greenhouse benches and the soil is kept saturated for 3 days. On the 3rd day, the containers are flooded to a level of 2–3 cm of water above the soil surface. The flooded soil surface is then treated with selected aqueous acetone (20/80 v/v water/acetone) mixtures and sufficient test compound to provide the equivalent of about 4.0 kg/ha to 0.50 kg/ha of active ingredient. After treatment, the containers are kept on greenhouse benches and watered such that the water level is maintained at 2–3 cm above the soil surface.

Three to four weeks after treatment, the plants are evaluated and rated for herbicidal effect based on visual determination of stand, size, vigor, chlorosis, growth malformation and overall appearance. The rating system used is shown below. If more than one test is run, the data are averaged. The results are reported in Table III.

| RATING SYSTEM USED | | |
|---|---|---|
| Rating | Meaning | % Control Compared to Check |
| 0 | No Effect | 0 |
| 1 | Trace Effect | 1–5 |
| 2 | Slight Effect | 6–15 |
| 3 | Moderate Effect | 16–29 |
| 4 | Injury | 30–44 |
| 5 | Definite Injury | 45–64 |
| 6 | Herbicidal Effect | 65–79 |
| 7 | Good Herbicidal Effect | 80–90 |
| 8 | Approaching Complete Kill | 91–99 |
| 9 | Complete Kill | 100 |
| — | Not Tested | |

| PLANT SPECIES USED | | |
|---|---|---|
| Abbreviation | Common Name | Scientific Name |
| ECHCG | Barnyard Grass | *Echinochloa crus-galli* (L.) Beauv. |
| ECHORC | Water Grass | *Echinochloa oryzoides* (ARD.) Fritsch |
| ORYSAT | Rice, Tebonnet | *Oryza sativa*, L. CV. Tebonnet |

TABLE III

PREEMERGENCE/POST-TRANSPLANT EVALUATION

| Example No. | Rate kg/ha | ECHCG | ECHORC | ORYSAT |
|---|---|---|---|---|
| 8 | 2.0 | 9.0 | — | 0.0 |
|   | 1.0 | 9.0 | 9.0 | 0.3 |
|   | 0.5 | 9.0 | 9.0 | 0.3 |
| 9 | 1.0 | 9.0 | — | 1.5 |
|   | 0.5 | 9.0 | — | 1.5 |
| 10 | 1.0 | 9.0 | 9.0 | 0.0 |
|   | 0.5 | 9.0 | 9.0 | 0.0 |
| 12 | 1.0 | — | 9.0 | 0.0 |
|   | 0.5 | — | 8.0 | 0.0 |
| 21 | 1.0 | 8.0 | — | 0.0 |
|   | 0.5 | 7.0 | — | 0.0 |
| 22 | 1.0 | 9.0 | — | 0.5 |
|   | 0.5 | 9.0 | — | 0.5 |
| 23 | 1.0 | 0.0 | — | 0.0 |
|   | 0.5 | 0.0 | — | 0.0 |
| 24 | 1.0 | 9.0 | — | 2.0 |
|   | 0.5 | 9.0 | — | 2.0 |
| 25 | 1.0 | — | 6.0 | 0.0 |
|   | 0.5 | — | 2.0 | 0.0 |

TABLE III-continued

PREEMERGENCE/POST-TRANSPLANT EVALUATION

| Example No. | Rate kg/ha | ECHCG | ECHORC | ORYSAT |
|---|---|---|---|---|
| 29 | 1.0 | 7.0 | — | 3.0 |
|  | 0.5 | 7.0 | — | 2.0 |
| 30 | 1.0 | 9.0 | — | 0.5 |
|  | 0.5 | 9.0 | — | 0.3 |
| 31 | 1.0 | 9.0 | — | 0.0 |
|  | 0.5 | 9.0 | — | 0.0 |
| 32 | 1.0 | 9.0 | — | 0.0 |
|  | 0.5 | 9.0 | — | 0.0 |
| 33 | 1.0 | 0.0 | — | 0.0 |
|  | 0.5 | 0.0 | — | 0.0 |
| 34 | 4.0 | 9.0 | — | 0.0 |
|  | 1.0 | 9.0 | 9.0 | 0.0 |
|  | 0.5 | 9.0 | 7.0 | 0.0 |
| 38 | 1.0 | 8.0 | — | 0.0 |
|  | 0.5 | 7.0 | — | 0.0 |
| 39 | 1.0 | 7.0 | — | 0.0 |
|  | 0.5 | 7.0 | — | 0.0 |
| 40 | 1.0 | 9.0 | — | 0.0 |
|  | 0.5 | 6.0 | — | 0.0 |
| 41 | 1.0 | 9.0 | — | 0.0 |
|  | 0.5 | 9.0 | — | 0.0 |
| 42 | 1.0 | 0.0 | — | 0.0 |
|  | 0.5 | 0.0 | — | 0.0 |
| 43 | 1.0 | 8.0 | — | 1.0 |
|  | 0.5 | 7.0 | — | 0.0 |
| 44 | 1.0 | 9.0 | — | 0.0 |
|  | 0.5 | 7.0 | — | 0.0 |
| 45 | 1.0 | 9.0 | — | 0.0 |
|  | 0.5 | 9.0 | — | 0.0 |
| 46 | 1.0 | 1.0 | — | 0.0 |
|  | 0.5 | 0.0 | — | 0.0 |
| 47 | 1.0 | 0.0 | — | 0.0 |
|  | 0.5 | 0.0 | — | 0.0 |
| 48 | 1.0 | 0.0 | — | 0.0 |
|  | 0.5 | 0.0 | — | 0.0 |
| 49 | 1.0 | — | 9.0 | 0.0 |
|  | 0.5 | — | 9.0 | 0.0 |
| 50 | 1.0 | — | 9.0 | 0.0 |
|  | 0.5 | — | 9.0 | 0.0 |
| 51 | 1.0 | — | 9.0 | 0.0 |
|  | 0.5 | — | 9.0 | 0.0 |
| 52 | 4.0 | 3.0 | — | 0.0 |
|  | 1.0 | 7.0 | 0.0 | 0.0 |
|  | 0.5 | 2.0 | 0.0 | 0.0 |
| 53 | 4.0 | 0.0 | — | 0.0 |
|  | 1.0 | 2.0 | — | 0.0 |
|  | 0.5 | 1.0 | — | 0.0 |
| 54 | 1.0 | 0.0 | — | 0.0 |
|  | 0.5 | 0.0 | — | 0.0 |
| 55 | 1.0 | 9.0 | 9.0 | 0.0 |
|  | 0.5 | 9.0 | 9.0 | 0.0 |
| 56 | 1.0 | 9.0 | — | 0.0 |
|  | 0.5 | 8.0 | — | 0.0 |
| 57 | 1.0 | 9.0 | — | 0.0 |
|  | 0.5 | 9.0 | — | 0.0 |
| 58 | 1.0 | 9.0 | — | 0.0 |
|  | 0.5 | 9.0 | — | 0.0 |
| 59 | 1.0 | 0.0 | — | 0.0 |
|  | 0.5 | 0.0 | — | 0.0 |
| 60 | 1.0 | 9.0 | — | 0.0 |
|  | 0.5 | 9.0 | — | 0.0 |
| 61 | 1.0 | 2.0 | — | 0.0 |
|  | 0.5 | 1.0 | — | 0.0 |
| 62 | 1.0 | 0.0 | — | 0.0 |
|  | 0.5 | 0.0 | — | 0.0 |
| 63 | 1.0 | 9.0 | — | 0.0 |
|  | 0.5 | 9.0 | — | 0.0 |
| 64 | 1.0 | 0.0 | — | 0.0 |
|  | 0.5 | 0.0 | — | 0.0 |
| 65 | 1.0 | 9.0 | 9.0 | 0.0 |
|  | 0.5 | 9.0 | 9.0 | 0.0 |
| 66 | 1.0 | 7.0 | — | 0.0 |
|  | 0.5 | 1.0 | — | 0.0 |
| 67 | 1.0 | 9.0 | — | 0.0 |
|  | 0.5 | 6.0 | — | 0.0 |
| 68 | 1.0 | 0.0 | — | 0.0 |
|  | 0.5 | 0.0 | — | 0.0 |
| 69 | 1.0 | 9.0 | — | 0.0 |
|  | 0.5 | 9.0 | — | 0.0 |
| 70 | 1.0 | 9.0 | — | 0.0 |
|  | 0.5 | 9.0 | — | 0.0 |
| 71 | 1.0 | 0.0 | — | 0.0 |
|  | 0.5 | 0.0 | — | 0.0 |
| 72 | 1.0 | 9.0 | — | 0.0 |
|  | 0.5 | 9.0 | — | 0.0 |
| 73 | 1.0 | 0.0 | — | 0.0 |
|  | 0.5 | 0.0 | — | 0.0 |
| 74 | 1.0 | 9.0 | — | 0.0 |
|  | 0.5 | 9.0 | — | 0.0 |
| 75 | 1.0 | 0.0 | — | 0.0 |
|  | 0.5 | 0.0 | — | 0.0 |
| 76 | 1.0 | 4.0 | — | 0.0 |
|  | 0.5 | 2.0 | — | 0.0 |
| 77 | 1.0 | 0.0 | — | 0.0 |
|  | 0.5 | 0.0 | — | 0.0 |
| 78 | 1.0 | — | 0.0 | 0.0 |
|  | 0.5 | — | 0.0 | 0.0 |
| 79 | 1.0 | — | 9.0 | 0.0 |
|  | 0.5 | — | 9.0 | 0.0 |
| 80 | 1.0 | — | 0.0 | 0.0 |
|  | 0.5 | — | 0.0 | 0.0 |
| 81 | 1.0 | — | 0.0 | 0.0 |
|  | 0.5 | — | 0.0 | 0.0 |
| 82 | 1.0 | — | 9.0 | 0.0 |
|  | 0.5 | — | 8.0 | 0.0 |
| 83 | 1.0 | — | 0.0 | 0.0 |
|  | 0.5 | — | 0.0 | 0.0 |
| 84 | 1.0 | — | 6.0 | 0.0 |
|  | 0.5 | — | 1.0 | 0.0 |
| 85 | 1.0 | 9.0 | — | 0.0 |
|  | 0.5 | 9.0 | — | 0.0 |
| 86 | 1.0 | 9.0 | 9.0 | 0.0 |
|  | 0.5 | 9.0 | 9.0 | 0.0 |
| 87 | 4.0 | 9.0 | — | 0.0 |
|  | 1.0 | 9.0 | 9.0 | 0.0 |
|  | 0.5 | 9.0 | 9.0 | 0.0 |
| 88 | 1.0 | 7.0 | — | 0.0 |
|  | 0.5 | 6.0 | — | 0.0 |
| 89 | 1.0 | 6.0 | — | 0.0 |
|  | 0.5 | 6.0 | — | 0.0 |
| 90 | 1.0 | 4.5 | — | 0.0 |
|  | 0.5 | 3.5 | — | 0.0 |
| 91 | 1.0 | 9.0 | — | 0.0 |
|  | 0.5 | 9.0 | — | 0.0 |
| 92 | 1.0 | 2.0 | — | 0.0 |
|  | 0.5 | 2.0 | — | 0.0 |
| 93 | 1.0 | 9.0 | — | 0.0 |
|  | 0.5 | 9.0 | 9.0 | 0.0 |
| 94 | 1.0 | 9.0 | — | 0.0 |
|  | 0.5 | 9.0 | 9.0 | 0.0 |
| 95 | 1.0 | — | 9.0 | 0.0 |
|  | 0.5 | — | 9.0 | 0.0 |
| 101 | 1.0 | — | 9.0 | 0.0 |
|  | 0.5 | — | 9.0 | 0.0 |
| 110 | 1.0 | — | 8.5 | 0.0 |
|  | 0.5 | — | 8.0 | 0.0 |
| 111 | 1.0 | — | 9.0 | 0.0 |
|  | 0.5 | — | 9.0 | 0.0 |
| 114 | 2.0 | — | 0.0 | 0.0 |
|  | 1.0 | — | 0.0 | 0.0 |
|  | 0.5 | — | 0.0 | 0.0 |
| 116 | 1.0 | — | 5.5 | 0.0 |
|  | 0.5 | — | 1.5 | 0.0 |
| 117 | 2.0 | — | 7.0 | 4.0 |
|  | 1.0 | — | 7.0 | 3.0 |
|  | 0.5 | — | 3.0 | 0.5 |
| 121 | 1.0 | — | 9.0 | 2.0 |
|  | 0.5 | — | 9.0 | 1.0 |

TABLE III-continued

PREEMERGENCE/POST-TRANSPLANT EVALUATION

| Example No. | Rate kg/ha | ECHCG | ECHORC | ORYSAT |
|---|---|---|---|---|
| 122 | 1.0 | — | 9.0 | 0.0 |
|  | 0.5 | — | 9.0 | 0.0 |
| 127 | 1.0 | — | 0.0 | 0.0 |
|  | 0.5 | — | 0.0 | 0.0 |
| 133 | 1.0 | — | 9.0 | 0.0 |
|  | 0.5 | — | 9.0 | 0.0 |
| 136 | 1.0 | — | 9.0 | 0.0 |
|  | 0.5 | — | 9.0 | 0.5 |
| 137 | 1.0 | — | 9.0 | 0.0 |
|  | 0.5 | — | 9.0 | 0.2 |
| 138 | 2.0 | — | 9.0 | 4.0 |
|  | 1.0 | — | 9.0 | 0.0 |
|  | 0.5 | — | 9.0 | 0.0 |
| 139 | 1.0 | — | 9.0 | 0.0 |
|  | 0.5 | — | 9.0 | 0.0 |
| 148 | 1.0 | — | 0.0 | 0.0 |
|  | 0.5 | — | 0.0 | 0.0 |
| 155 | 1.0 | — | 9.0 | 0.0 |
|  | 0.5 | — | 9.0 | 0.0 |
| 156 | 1.0 | — | 9.0 | 0.0 |
|  | 0.5 | — | 9.0 | 0.0 |
| 157 | 1.0 | — | 9.0 | 0.0 |
|  | 0.5 | — | 9.0 | 0.0 |
| 172 | 1.0 | — | 9.0 | 0.0 |
|  | 0.5 | — | 8.5 | 0.0 |
| 173 | 1.0 | — | 8.0 | 0.0 |
|  | 0.5 | — | 8.0 | 0.0 |
| 174 | 1.0 | — | 9.0 | 0.0 |
|  | 0.5 | — | 9.0 | 0.0 |
| 175 | 1.0 | — | 9.0 | 0.0 |
|  | 0.5 | — | 9.0 | 0.0 |
| 176 | 1.0 | — | 9.0 | 0.0 |
|  | 0.5 | — | 9.0 | 0.0 |
| 177 | 1.0 | — | 7.0 | 0.0 |
|  | 0.5 | — | 5.5 | 0.0 |
| 192 | 1.0 | — | 9.0 | 0.0 |
|  | 0.5 | — | 9.0 | 0.0 |

EXAMPLE 197

Preemergence Herbicidal Evaluation Of Test Compounds In The Presence Of Transplanted Rice Under Flooded Paddy Conditions In this example, Deluvian paddy soil (Toyokawa paddy soil) is placed in plastic pots, 100 $cm^2 \times 9$ cm in depth. Water is added to the level of the soil surface in the pot and the mixture is paddled 3 cm in depth.

Pots are then variously sown with monocotyledenous weed seeds and tubers at 0–2 cm in soil depth, as well as transplanted rice plants at the 2.5 leaf stage. The rice plants are transplanted at about 3 cm soil depth. Water is then added to all of the pots to 3 cm deep and kept at a depth of 3 cm for the duration of the test. Test compounds are applied in the manner described in Example 96 two days after transplanting the rice plants and sowing the weed seeds and tubers. The pots are then placed on greenhouse benches and cared for in the conventional manner. Tests are evaluated at 20 and 30 days after treatment. Evaluations made at 30 days after treatment are shown on Table IV. The rating system used is the same as that described in Example 196.

PLANT SPECIES USED

| Abbreviation | Common Name | Scientific Name |
|---|---|---|
| ECHCG | Barnyard Grass | *Echinochloa crus-galli* |
| SAGPY | Arrowhead (Pygmaea) | *Sagittaria pygmaea* |
| CYPSE | Flatsedge, perennial | *Cyperus serotinus* |
| MOOVA | Monochoria | *Monochoria vaginalis* |
| CYPDI | Flatsedge, smallflower | *Cyperus difformis* |
| SCPJU | Bulrush, Japanese- | *Scirpus juncoides* |
| ORYSAK | Rice, Koshihikari | *Oryza sativa*, L. CV. Koshihikari |

TABLE IV

PREEMERGENCE/POST-TRANSPLANT EVALUATION

| Ex. No. | Rate ka/ha | ECHCG | SAGPY | CYPSE | MOOVA | CYPDI | SCPJU | ORYSAK |
|---|---|---|---|---|---|---|---|---|
| 8 | 1.0 | 9 | 2 | 2 | 9 | 9 | 8 | 0 |
|  | 0.5 | 9 | 1 | 0 | 9 | 9 | 7 | 0 |
| 9 | 1.0 | 7 | 0 | 0 | 1 | 2 | 0 | 0 |
|  | 0.5 | 6 | 0 | 0 | 0 | 0 | 0 | 0 |
| 10 | 1.0 | 9 | 2 | 0 | 9 | 9 | 5 | 0 |
|  | 0.5 | 9 | 0 | 0 | 8 | 9 | 4 | 0 |
| 12 | 1.0 | 9 | 0 | 0 | 7 | 3 | 0 | 0 |
|  | 0.5 | 9 | 0 | 0 | 6 | 2 | 0 | 0 |
| 21 | 1.0 | 8 | 0 | 7 | 3 | 5 | 0 | 0 |
|  | 0.5 | 7 | 0 | 2 | 0 | 3 | 0 | 0 |
| 22 | 1.0 | 9 | 1 | 1 | 9 | 8 | 7 | 0 |
|  | 0.5 | 9 | 0 | 0 | 8 | 7 | 5 | 0 |
| 23 | 2.0 | 9 | 0 | 0 | 3 | 2 | 2 | 0 |
|  | 1.0 | 6 | 0 | 0 | 0 | 0 | 0 | 0 |
|  | 0.5 | 4 | 0 | 0 | 0 | 0 | 0 | 0 |
| 25 | 1.0 | 9 | 0 | 0 | 9 | 6 | 3 | 0 |
|  | 0.5 | 9 | 0 | 0 | 8 | 3 | 0 | 0 |
| 31 | 1.0 | 9 | 0 | 4 | 7 | 7 | 3 | 0 |
|  | 0.5 | 9 | 0 | 0 | 7 | 6 | 0 | 0 |
| 32 | 1.0 | 9 | 0 | 2 | 8 | 8 | 2 | 0 |
|  | 0.5 | 9 | 0 | 1 | 7 | 7 | 0 | 0 |
| 33 | 2.0 | 6 | 9 | 9 | 9 | 9 | 7 | 8 |
|  | 1.0 | 4 | 8 | 9 | 9 | 9 | 6 | 8 |
|  | 0.5 | 2 | 7 | 9 | 9 | 8 | 5 | 5 |
| 35 | 2.0 | 8 | 2 | 0 | 0 | 1 | 0 | 0 |

TABLE IV-continued

PREEMERGENCE/POST-TRANSPLANT EVALUATION

| Ex. No. | Rate ka/ha | ECHCG | SAGPY | CYPSE | MOOVA | CYPDI | SCPJU | ORYSAK |
|---|---|---|---|---|---|---|---|---|
|  | 1.0 | 8 | 0 | 0 | 0 | 0 | 0 | 0 |
|  | 0.5 | 7 | 0 | 0 | 0 | 0 | 0 | 0 |
| 38 | 1.0 | 8 | 0 | 0 | 0 | 0 | 0 | 0 |
|  | 0.5 | 6 | 0 | 0 | 0 | 0 | 0 | 0 |
| 39 | 1.0 | 7 | 0 | 0 | 0 | 0 | 0 | 0 |
|  | 0.5 | 5 | 0 | 0 | 0 | 0 | 0 | 0 |
| 40 | 1.0 | 9 | 0 | 0 | 0 | 0 | 0 | 0 |
|  | 0.5 | 9 | 0 | 0 | 0 | 0 | 0 | 0 |
| 41 | 1.0 | 9 | 1 | 7 | 8 | 9 | 2 | 1 |
|  | 0.5 | 9 | 0 | 3 | 7 | 7 | 1 | 0 |
| 42 | 2.0 | 2 | 0 | 0 | 0 | 0 | 0 | 0 |
|  | 1.0 | 0 | 0 | 0 | 0 | 0 | 0 | 0 |
|  | 0.5 | 0 | 0 | 0 | 0 | 0 | 0 | 0 |
| 43 | 1.0 | 8 | 0 | 0 | 0 | 0 | 0 | 0 |
|  | 0.5 | 6 | 0 | 0 | 0 | 0 | 0 | 0 |
| 44 | 1.0 | 8 | 0 | 0 | 0 | 0 | 0 | 0 |
|  | 0.5 | 5 | 0 | 0 | 0 | 0 | 0 | 0 |
| 45 | 1.0 | 7 | 0 | 0 | 0 | 0 | 0 | 0 |
|  | 0.5 | 4 | 0 | 0 | 0 | 0 | 0 | 0 |
| 46 | 2.0 | 0 | 0 | 0 | 0 | 0 | 0 | 0 |
|  | 1.0 | 0 | 0 | 0 | 0 | 0 | 0 | 0 |
| 47 | 2.0 | 0 | 0 | 0 | 0 | 0 | 0 | 0 |
|  | 1.0 | 0 | 0 | 0 | 0 | 0 | 0 | 0 |
| 48 | 2.0 | 0 | 0 | 0 | 0 | 0 | 0 | 0 |
|  | 1.0 | 0 | 0 | 0 | 0 | 0 | 0 | 0 |
| 49 | 1.0 | 9 | 0 | 9 | 9 | 9 | 8 | 0 |
|  | 0.5 | 9 | 0 | 2 | 9 | 8 | 5 | 0 |
| 50 | 1.0 | 9 | 0 | 0 | 8 | 8 | 1 | 0 |
|  | 0.5 | 9 | 0 | 0 | 8 | 7 | 0 | 0 |
| 51 | 1.0 | 9 | 0 | 2 | 8 | 7 | 0 | 0 |
|  | 0.5 | 8 | 0 | 0 | 8 | 5 | 0 | 0 |
| 55 | 1.0 | 9 | 1 | 9 | 9 | 9 | 9 | 0 |
|  | 0.5 | 9 | 0 | 8 | 9 | 9 | 8 | 0 |
| 56 | 1.0 | 8 | 0 | 0 | 3 | 2 | 0 | 0 |
|  | 0.5 | 6 | 0 | 0 | 2 | 1 | 0 | 0 |
| 57 | 1.0 | 9 | 0 | 2 | 2 | 2 | 0 | 0 |
|  | 0.5 | 9 | 0 | 0 | 1 | 1 | 0 | 0 |
| 58 | 1.0 | 9 | 0 | 0 | 4 | 3 | 0 | 0 |
|  | 0.5 | 9 | 0 | 0 | 2 | 1 | 0 | 0 |
| 59 | 1.0 | 5 | 0 | 0 | 1 | 2 | 2 | 0 |
|  | 0.5 | 3 | 0 | 0 | 0 | 0 | 0 | 0 |
| 60 | 1.0 | 9 | 0 | 5 | 6 | 5 | 0 | 0 |
|  | 0.5 | 9 | 0 | 0 | 5 | 3 | 0 | 0 |
| 61 | 1.0 | 4 | 0 | 0 | 1 | 1 | 0 | 0 |
|  | 0.5 | 3 | 0 | 0 | 0 | 0 | 0 | 0 |
| 62 | 1.0 | 2 | 0 | 0 | 0 | 0 | 0 | 0 |
|  | 0.5 | 0 | 0 | 0 | 0 | 0 | 0 | 0 |
| 63 | 1.0 | 9 | 0 | 0 | 2 | 1 | 1 | 0 |
|  | 0.5 | 9 | 0 | 0 | 1 | 0 | 0 | 0 |
| 64 | 1.0 | 1 | 0 | 0 | 0 | 0 | 0 | 0 |
|  | 0.5 | 0 | 0 | 0 | 0 | 0 | 0 | 0 |
| 65 | 1.0 | 9 | 4 | 5 | 9 | 9 | 2 | 1 |
|  | 0.5 | 9 | 2 | 2 | 9 | 9 | 0 | 0 |
| 66 | 1.0 | 9 | 0 | 0 | 2 | 2 | 0 | 0 |
|  | 0.5 | 8 | 0 | 0 | 0 | 0 | 0 | 0 |
| 67 | 1.0 | 9 | 0 | 1 | 2 | 3 | 0 | 1 |
|  | 0.5 | 8 | 0 | 0 | 0 | 2 | 0 | 0 |
| 68 | 1.0 | 0 | 0 | 0 | 0 | 0 | 0 | 0 |
|  | 0.5 | 0 | 0 | 0 | 0 | 0 | 0 | 0 |
| 69 | 1.0 | 9 | 0 | 2 | 7 | 7 | 2 | 1 |
|  | 0.5 | 9 | 0 | 0 | 6 | 6 | 0 | 0 |
| 70 | 1.0 | 9 | 0 | 5 | 2 | 1 | 0 | 0 |
|  | 0.5 | 9 | 0 | 0 | 0 | 0 | 0 | 0 |
| 71 | 1.0 | 6 | 0 | 0 | 0 | 0 | 0 | 0 |
|  | 0.5 | 5 | 0 | 0 | 0 | 0 | 0 | 0 |
| 72 | 1.0 | 9 | 0 | 1 | 7 | 4 | 0 | 0 |
|  | 0.5 | 9 | 0 | 0 | 3 | 2 | 0 | 0 |
| 73 | 1.0 | 7 | 0 | 2 | 0 | 0 | 0 | 0 |
|  | 0.5 | 3 | 0 | 0 | 0 | 0 | 0 | 0 |
| 74 | 1.0 | 9 | 0 | 0 | 4 | 6 | 2 | 0 |
|  | 0.5 | 9 | 0 | 0 | 2 | 3 | 0 | 0 |
| 75 | 1.0 | 4 | 0 | 0 | 2 | 1 | 0 | 0 |
|  | 0.5 | 2 | 0 | 0 | 0 | 0 | 0 | 0 |
| 76 | 1.0 | 7 | 0 | 0 | 2 | 1 | 1 | 0 |

TABLE IV-continued

PREEMERGENCE/POST-TRANSPLANT EVALUATION

| Ex. No. | Rate ka/ha | ECHCG | SAGPY | CYPSE | MOOVA | CYPDI | SCPJU | ORYSAK |
|---|---|---|---|---|---|---|---|---|
|  | 0.5 | 6 | 0 | 0 | 0 | 0 | 0 | 0 |
| 77 | 1.0 | 6 | 0 | 0 | 2 | 0 | 0 | 0 |
|  | 0.5 | 6 | 0 | 0 | 1 | 0 | 0 | 0 |
| 78 | 1.0 | 2 | 1 | 4 | 2 | 0 | 6 | 0 |
|  | 0.5 | 0 | 0 | 2 | 1 | 0 | 4 | 0 |
| 79 | 1.0 | 9 | 2 | 0 | 9 | 9 | 7 | 0 |
|  | 0.5 | 9 | 1 | 0 | 8 | 7 | 6 | 0 |
| 85 | 1.0 | 9 | 0 | 0 | 4 | 4 | 2 | 0 |
|  | 0.5 | 7 | 0 | 0 | 1 | 2 | 1 | 0 |
| 86 | 1.0 | 9 | 5 | 5 | 9 | 9 | 9 | 0 |
|  | 0.5 | 9 | 2 | 2 | 9 | 9 | 8 | 0 |
| 87 | 1.0 | 9 | 0 | 4 | 8 | 8 | 4 | 0 |
|  | 0.5 | 9 | 0 | 2 | 7 | 8 | 2 | 0 |
| 88 | 1.0 | 5 | 0 | 0 | 0 | 0 | 0 | 0 |
|  | 0.5 | 4 | 0 | 0 | 0 | 0 | 0 | 0 |
| 89 | 1.0 | 4 | 0 | 0 | 0 | 0 | 0 | 0 |
|  | 0.5 | 2 | 0 | 0 | 0 | 0 | 0 | 0 |
| 90 | 1.0 | 3 | 0 | 0 | 0 | 0 | 0 | 0 |
|  | 0.5 | 0 | 0 | 0 | 0 | 0 | 0 | 0 |
| 91 | 1.0 | 9 | 0 | 0 | 5 | 8 | 0 | 0 |
|  | 0.5 | 9 | 0 | 0 | 3 | 5 | 0 | 0 |
| 93 | 1.0 | 9 | 0 | 2 | 9 | 9 | 7 | 0 |
|  | 0.5 | 9 | 0 | 0 | 8 | 8 | 5 | 0 |
| 94 | 1.0 | 9 | 0 | 7 | 9 | 9 | 8 | 0 |
|  | 0.5 | 9 | 0 | 3 | 9 | 9 | 5 | 0 |
| 116 | 0.50 | 7 | 6 | 3 | 2 | 8 | 6 | 0 |
|  | 0.25 | 5 | 4 | 1 | 0 | 7 | 5 | 0 |
| 117 | 0.50 | 7 | 2 | 5 | 4 | 8 | 7 | 1 |
|  | 0.25 | 5 | 1 | 2 | 0 | 7 | 6 | 1 |
| 119 | 0.50 | 9 | 2 | 0 | 0 | 2 | 0 | 0 |
|  | 0.25 | 8 | 0 | 0 | 0 | 1 | 0 | 0 |
| 120 | 0.50 | 9 | 0 | — | 6 | 9 | 8 | 0 |
|  | 0.25 | 9 | 0 | — | 2 | 9 | 7 | 0 |
| 121 | 0.50 | 9 | 0 | 3 | 5 | 9 | 8 | 0 |
|  | 0.25 | 9 | 0 | 0 | 2 | 9 | 6 | 0 |
| 122 | 0.50 | 9 | 4 | 0 | 0 | 9 | 5 | 0 |
|  | 0.25 | 9 | 2 | 0 | 0 | 9 | 3 | 0 |
| 123 | 0.50 | 9 | 0 | 0 | 0 | 9 | 7 | 0 |
|  | 0.25 | 9 | 0 | 0 | 0 | 7 | 5 | 0 |
| 124 | 0.50 | 9 | 2 | 0 | 0 | 9 | 7 | 0 |
|  | 0.25 | 9 | 0 | 0 | 0 | 9 | 6 | 0 |
| 125 | 0.50 | 9 | 0 | 2 | 5 | 9 | 9 | 0 |
|  | 0.25 | 9 | 0 | 0 | 2 | 9 | 6 | 0 |
| 126 | 0.50 | 9 | 2 | — | 3 | 7 | 6 | 0 |
|  | 0.25 | 9 | 2 | — | 2 | 3 | 2 | 0 |
| 136 | 0.50 | 9 | 0 | 0 | 2 | 7 | 5 | 0 |
|  | 0.25 | 9 | 0 | 0 | 0 | 6 | 4 | 0 |
| 137 | 0.50 | 9 | 0 | 2 | 7 | 9 | 9 | 0 |
|  | 0.25 | 9 | 0 | 1 | 7 | 9 | 9 | 0 |
| 138 | 0.50 | 9 | 0 | 0 | 5 | 9 | 9 | 0 |
|  | 0.25 | 9 | 0 | 0 | 6 | 9 | 9 | 0 |
| 139 | 0.50 | 9 | 0 | 2 | 8 | 9 | 9 | 0 |
|  | 0.25 | 9 | 0 | 2 | 8 | 9 | 9 | 0 |
| 155 | 0.50 | 9 | 0 | 2 | 9 | 9 | 9 | 0 |
|  | 0.25 | 9 | 0 | — | 7 | 9 | 9 | 0 |

What is claimed is:

1. A compound of formula (I)

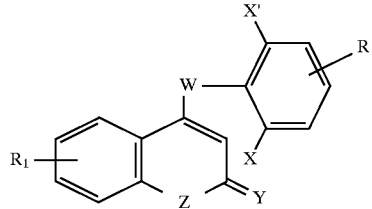

wherein

X and X' are each independently halogen, $C_1$–$C_4$ alkyl or $C_2$–$C_4$ alkenyl;

W and Y are each independently O or S and Z is O;

R is any combination of from one to three H, halogen, $C_1$–$C_4$ alkyl, $C_3$–$C_6$ cycloalkyl, $C_1$–$C_4$ haloalkyl or $C_1$–$C_4$ alkoxy groups; and $R_1$ is any combination of from one to four $NO_2$ groups.

2. The compound according to claim 1 wherein X and X' are each independently Cl, Br or $CH_3$ and W and Y are O.

3. The compound according to claim 2 wherein R is H and $R_1$ is one, two or three $NO_2$ groups.

4. The compound according to claim 3 wherein X and X' are Cl, Br or $CH_3$, R is H and $R_1$ is 5-$NO_2$.

5. The compound according to claim 4

4-(2,6-dichlorophenoxy)-6-methoxycoumarin;
4-(2,6-dibromophenoxy)-8-methoxycoumarin;
4-(2,6-dichlorophenoxy)-6,7-dimethoxycoumarin;
4-(2,6-dibromophenoxy)-6,7-dimethoxycoumarin;
4-(2,6-dichlorophenoxy)-5,6,7-trimethoxycoumarin;
4-(2,6-dibromophenoxy)-5,6,7-trimethoxycoumarin;
4-(2,6-dichlorophenoxy)-5-(trifluoromethyl)coumarin;
4-(2,6-dibromophenoxy)-5-(trifluoromethyl)coumarin;
4-[(2-chloro-6-methyl)phenoxy]-5-chlorocoumarin;
4-[(2-chloro-6-methyl)phenoxy]-5-chlorocoumarin;
4-(2,6-dibromophenoxy)-5-chlorocoumarin;
4-(2,6-dichlorophenoxy)-5-chlorocoumarin;
4-[(2-chloro-6-methyl)phenoxy]-5-fluorocoumarin;
4-(2,6-dichlorophenoxy)-5-fluorocoumarin;
4-(2,6-dichlorophenoxy)-5-methylcoumarin;
4-[(2-chloro-6-methyl)phenoxy]-5-methylcoumarin;
which is 4-(2,6-dichlorophenoxy)-5-nitrocoumarin.

6. A herbicidal composition which comprises an agronomically acceptable carrier and a compound of formula I

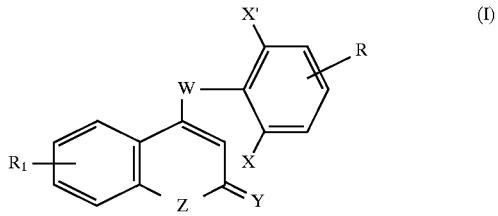

wherein X, X', W, Y, Z, R and $R_1$ are defined in claim 1.

7. The composition according to claim 6 wherein X and X' are each independently Cl, Br or $CH_3$ and W and Y are O.

8. The composition according to claim 7 wherein R is H and $R_1$ is one, two or three $NO_2$ groups.

* * * * *